(12) United States Patent
Shalayev et al.

(10) Patent No.: US 11,284,946 B2
(45) Date of Patent: Mar. 29, 2022

(54) ARTICULATING DRILL SYSTEM

(71) Applicant: THINK SURGICAL, INC., Fremont, CA (US)

(72) Inventors: Stan G. Shalayev, Fremont, CA (US); Joel F. Zuhars, Fremont, CA (US); Allen B. Kantrowitz, Fremont, CA (US); In K. Mun, Fremont, CA (US); Daniel Fuller, Fremont, CA (US); Simon R. Grover, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 323 days.

(21) Appl. No.: 16/659,153

(22) Filed: Oct. 21, 2019

(65) Prior Publication Data

US 2020/0046438 A1   Feb. 13, 2020

Related U.S. Application Data

(63) Continuation of application No. 15/512,180, filed as application No. PCT/US2015/051713 on Sep. 23, 2015, now Pat. No. 10,492,870.

(60) Provisional application No. 62/054,009, filed on Sep. 23, 2014.

(51) Int. Cl.
*A61B 34/20* (2016.01)
*A61B 17/16* (2006.01)
*A61B 90/00* (2016.01)
*A61B 90/30* (2016.01)

(52) U.S. Cl.
CPC .......... *A61B 34/20* (2016.02); *A61B 17/1624* (2013.01); *A61B 17/1626* (2013.01); *A61B 17/1691* (2013.01); *A61B 90/36* (2016.02); *A61B 2034/2048* (2016.02); *A61B 2034/2055* (2016.02); *A61B 2034/2065* (2016.02); *A61B 2090/309* (2016.02)

(58) Field of Classification Search
CPC combination set(s) only.
See application file for complete search history.

(56) References Cited

U.S. PATENT DOCUMENTS

| 6,723,106 | B1 | 4/2004 | Charles et al. |
| 8,876,830 | B2 | 11/2014 | Hodorek et al. |
| 9,060,794 | B2 | 6/2015 | Kang et al. |
| 2005/0165420 | A1 | 7/2005 | Cha |

(Continued)

OTHER PUBLICATIONS

U.S. Appl. No. 61/318,537, filed Mar. 29, 2010; Title "Automatically Stabilized Bone Resection Tool", inventors Joel Zuhars and Jody L. Claypool.

(Continued)

*Primary Examiner* — Sameh R Boles
(74) *Attorney, Agent, or Firm* — Blue Filament Law PLLC

(57) ABSTRACT

An articulating drill system is provided that includes a hand-held portion and a drill portion. At least two actuators are provided for controlling at least two axes of the drill portion. A navigation system is provided to control the at least two actuators. In some embodiments, a tool is provided with the drill portion and adapted to interact with patient tissue. The drill portion can be modified to include at least two rigid objects in communication with the actuators and attached to the drill portion. The system can be used to make any linear cut within a deviation of ±1.0 mm and ±1.0°, or better in patient tissue.

18 Claims, 10 Drawing Sheets

(56) References Cited

U.S. PATENT DOCUMENTS

| | | | |
|---|---|---|---|
| 2005/0171553 A1 | 8/2005 | Schwarz et al. | |
| 2007/0034731 A1 | 2/2007 | Falco | |
| 2011/0130761 A1 | 6/2011 | Plaskos | |
| 2011/0264107 A1 | 10/2011 | Nikou | |
| 2012/0143084 A1 | 6/2012 | Shoham | |
| 2013/0060278 A1* | 3/2013 | Bozung | A61B 17/1675 606/205 |
| 2013/0064427 A1 | 3/2013 | Picard et al. | |
| 2015/0182285 A1 | 7/2015 | Yen et al. | |

OTHER PUBLICATIONS

Claasen, Gontje C., Martin, Philippe, and Picard, Frederic "High-Bandwidth Low-Latency Tracking Using Optical and Inertial Sensors" Proceedings of the 5th International Conference on Automation, Robotics and Applications, Dec. 6-8, 2011, Wellington, New Zeland; © 2011 IEEE; pp. 366-371.

Claasen, Gontje C., Martin, Philippe, and Picard, Frederic "Optical-Inertial Tracking System with High Bandwith and Low Latency" Proceedings of the 5th International Conference on Automation, Robotics and Applications; © 2011 EEE; pp. 171-181.

Claasen, G.C., Martin, P., and Picard, F. "Hybrid Optical-Inertial Tracking System for a Servo-Controlled Handheld Tool" Journal of Bone & Joint Surgery, British Volume, www.bjjprocs.boneandjoint.org.uk; dated Aug. 11, 2014; J Bone Joint Surg Br 2012 vol. 94-B No. SUPP XLIV 51; p. 1/2-2/2.

Claasen, Gontje C., Martin, Philippe, and Picard, Frederic "Tracking and Control for Handheld Surgery Tools"; Biomedical Circuits and Systems Conference (BioCAS), 2011; pp. 428-431; 978-1-4577-1470-2/11/$26.00 © 2011 IEEE.

Brisson, Gabriel, Kanade, Takeo, Digioia, Anthony, and Jaramaz, Branislav "Precision Freehand Sculpting of Bone"; pp. 1-8; The Robotic Institute, Carnegie Mellon University, Pittsburgh PA, USA; (brisson,tk)@cs.cmu.edu; The Institute for Computer Assisted Orthopaedic Surgery, The Western Pennsylvania Hospital, Pittsburgh, PA, USA. (tony, branko)@icaos.org; C. Barillot, D.R. Haynor, and P. Hellier (Eds.): MICCAI 2004, LNCS 3217, pp. 105-112, 2004, © Springer-Verlag Berlin Heidelberg 2004.

Tobergte, Andreas, Pomarlan, Mihai, and Hirzinger, Gerd "Robust Multi Sensor Pose Estimation for Medical Applications"; Institute of Robotics and Mechatronics, German Aerospace (DLR), 82234 Wessling, Germany; andreas.tobergte@dlr.de; pp. 105-112.

Kopfle, A., Schill, M., Rautmann, M., Schwarz, M.L.R., Pott, P.P., Wagner, A., Manner, R., Badreddin, E., Weiser, P., and Scharf, H.P. "Occlusion-Robust, Low-Latency Optical Tracking Using a Modular Scalable System Architecture"; Advanced Navigation and Motion Tracking II, Thursday, 17:00, N5; pp. 18.

El-Shenawy, Ahmed, Wagner, Achim, Pott, Peter, Gundling, Ralf, Schwarz, MarKus, Badreddin, Essam "Disturbance Attenuation of a Handheld Parallel Robot"; 2013 IEEE International Conference on Robotics and Automation (ICRA) Karlsruhe, Germany, May 6-10, 2013; pp. 4647-4652; 978-1-4673-5/13/$31.00 @2013 IEEE.

Devos, Thomas, Martin, Philippe, Picard Frederic JM, Borchers, Marco, Cabanial, Nicolas, and Dassier, Aude "A Hand-held computer-controlled tool for total knee replacement"; 5th Annual Meeting of the International Society for Computer Assisted Orthopaedic Surgery CAOS (2005); pp. 88-89.

Wagner, A., Pott, P.P, Scwarz, M.L., Scharf, H.P., Weiser, P., Kopfle, A. Manner, R. and Badreddin, E. "Control of a Handheld Robot for Orthopedic Surgery"; 3rd IFAC 2004; Department of Orthopedic Surgery, Faculty of Clinical Medicine, Mannheim, University Heidelberg, Germany; Institute of CAE, University of Applied Sciences Mannheim, Germany; Institute of Computer Science V, University of Mannheim, Germany; Automation Laboratory, University of Mannheim, Germany; pp. 1-6.

\* cited by examiner

ARTICULATING DRILL SYSTEM

RELATED APPLICATIONS

This application is a continuation of U.S. application Ser. No. 15/512,180 filed 17 Mar. 2017; now U.S. Pat. No. 10,492,870B1 that in turn is a U.S. National Phase Application of Ser. No. PCT/US2015/051713 filed 23 Sep. 2015 that in turn claims priority benefit of U.S. Provisional Application Ser. No. 62/054,009 filed 23 Sep. 2014; the contents of which are hereby incorporated by reference.

TECHNICAL FIELD

The present invention relates generally to computer-aided drill systems, and more specifically to a new and useful system for assisting with surgical procedures.

BACKGROUND

In thoracic surgery, the chest cavity often must be opened and the ribs retracted. Typically, oscillating saws are used to create an arcuate cut through the sternum, since it is difficult to properly close and reinforce a linear sternal cut for optimal cut planes consolidation, owing in part to the lack of a definitive reference or anchoring multiplanar structure to aid in sealing the closure. Cutting an arcuate line, however, is practically difficult and inexact with existing devices. Ideally, the sternum should be cut in a pattern where the two halves of the divided sternum can reunite in a manner that maximizes stability and surface area contact for primary osseous healing with maximal available osseous points and elements.

Freehand cutting saws or drills may be operated to cut such patterns like a triangle continuous wave that is commonly and synonymously referred to herein as "zig-zag" pattern. However, such free form incision patterns are inexact, prone to miss-cuts and suffer from vibrational deviations. Other non-articulating systems exist with tracking mechanisms that display the position and orientation of the device on a monitor. This however requires the operator to constantly check a monitor during cutting and there is little assistance provided to prevent either a miscut, inadequate cut placement, or the ability to constrain movement according to a planned and/or pre-programmed cutting pattern.

Thus, there exists a need for a method and device that assists the operator in precisely cutting the sternum in a pattern, whereupon closure, the two halves are joined to provide superior stability and increased contact surface area to promote optimal bone healing. There further exists a need for a system which prevents a drill operator from deviating from a pre-indicated planned cutting path. There also exists a need for a drilling system that allows an operator to compensate for a cutting surface's movement while maintaining a precise cutting pattern through a subject's sternum.

SUMMARY OF THE INVENTION

An articulating drill system is provided that includes a hand-held portion and a drill portion. At least two actuators are provided for controlling at least two axes of the drill portion. A navigation system is provided to control the actuators. In some embodiments, a tool is provided with the drill portion and adapted to interact with patient tissue. The tool in some embodiments, can accurately mark specific areas on tissue for digitization and/or registration. A drill guard is provided in some embodiments to travel on the underside of a cutting surface preventing the drill from cutting any surfaces, including patient tissue, underneath the drill guard.

The navigation system in some embodiments provides real-time feedback to one of a position, orientation, or velocity of said drill portion. The real-time feedback can include information relating a surface to the drill portion as the device is being operated to be used by a controller to adjust the at least two actuators to compensate for surface movement or user's movement of the hand-held portion or prevent the operation of the device outside a pre-indicated pattern. In some embodiments, a user-feedback mechanism is provided, such as a trigger or a foot pedal. The user-feedback mechanism can be activated by a user to communicate to the navigation system and drill that a new fixed plane of motion is desired. In some embodiments, the hand-held portion includes an adapter for attaching a rigid reference guide that provides the user with a visual relationship between the plane of the reference guide relative to the plane of the drill portion.

The drill portion can be modified to include at least two rigid objects in communication with the actuators and attached to the drill portion.

The system can be used to make any linear cut within a deviation of ±1.0 mm and ±1.0°, or better in patient tissue.

In some embodiments, the linear cut cuts the sternum for thoracic surgery in a "triangle wave pattern".

BRIEF DESCRIPTION OF THE DRAWINGS

The present invention is further detailed with respect to the following drawings. These figures are not intended to limit the scope of the present invention but rather illustrate certain attributes thereof.

DESCRIPTION OF THE PREFERRED EMBODIMENTS

This invention disclosed herein describes an articulating hand-held drill system for precise cutting along any plane, but more particularly to create a precise and smooth pattern incision along a surface in general and in particular to a subject's sternum.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

Figure 1:
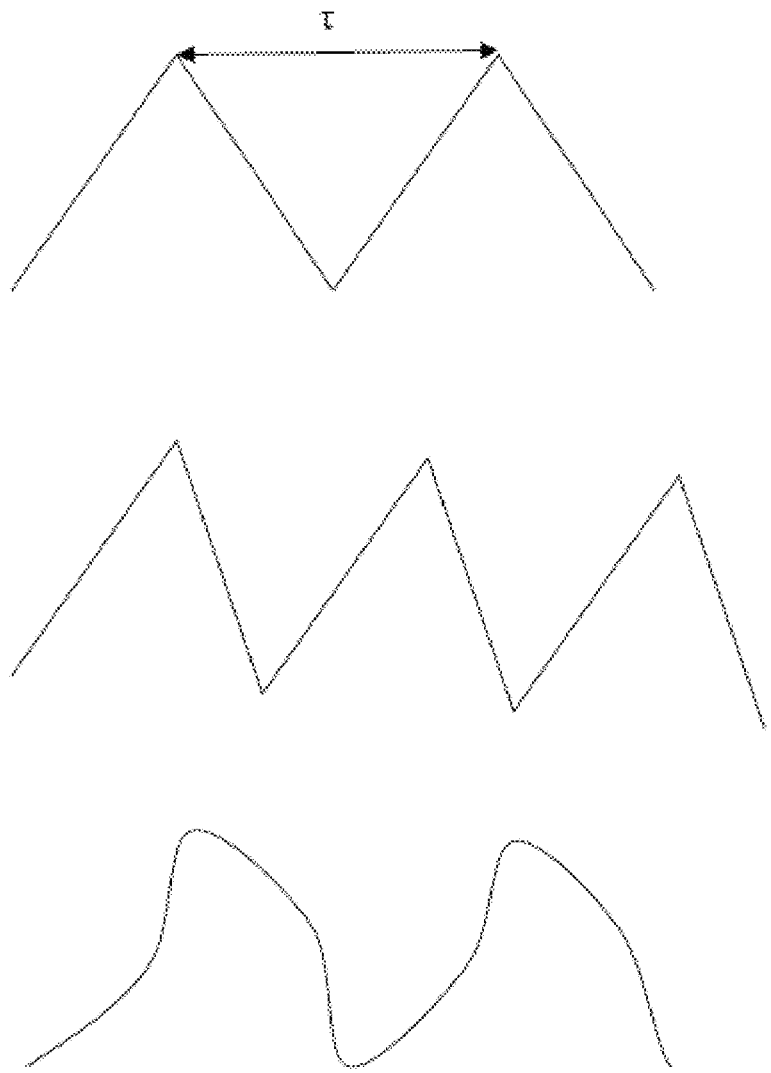
FIG. 1 are various exemplary triangle wave cut patterns produced by the present invention.
Figure 6:
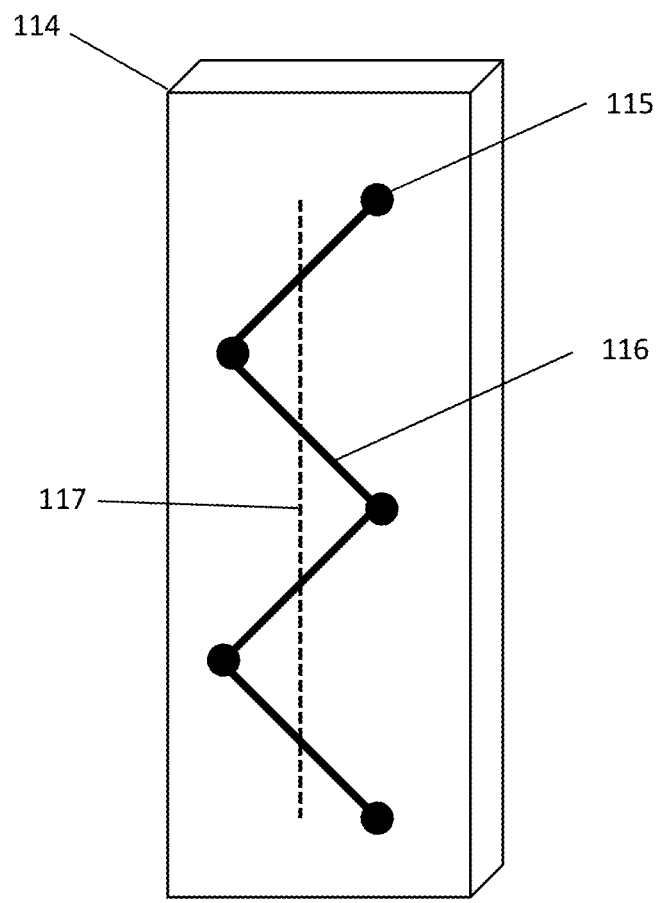
FIG. 6 is an exemplary cutting multiplanar path that can be created using the inventive system.

As used herein, a "triangle wave pattern" is defined to include at least one half of a period, of a triangle wave, saw tooth pattern, and variants thereof in which line segments of the patterns are arcuate between extrema. "Zigzag" is used herein synonymously with "triangle wave" with respect to incision patterns according to the present invention. Exemplary incision patterns according to the present invention are shown in FIG. 1 and FIG. 6 but are not meant to be limiting.

The invention described herein also represents a system which articulates to keep the drill in a fixed plane of motion during a cut through a surface after the cutting is started. It is appreciated that the fixed plane is maintained within a range of rotation of ±1° and translation of ±1 mm.

The invention disclosed herein further includes the usage of a navigation system comprised of trackable markers mounted on the device itself, the cutting target, otherwise providing a fixed reference frame in the incision field, or a combination of such marker positions. The usage and positioning of markers depends on factors that include: the degree of cutting target expected movement, the accuracy requirements for the cut, interfacing with the surgical navigation system, radiological subject's specific data sets, and the design and ergonomical features of the device.

One specific advantage of the present system is that the operator is able at any time to indicate to the system that the plane of cutting should change (i.e. from zig to zag).

The following description of the preferred embodiments of the invention is not intended to limit the invention to these preferred embodiments, but rather to enable any person skilled in the art to make and use this invention.

Figure 2:
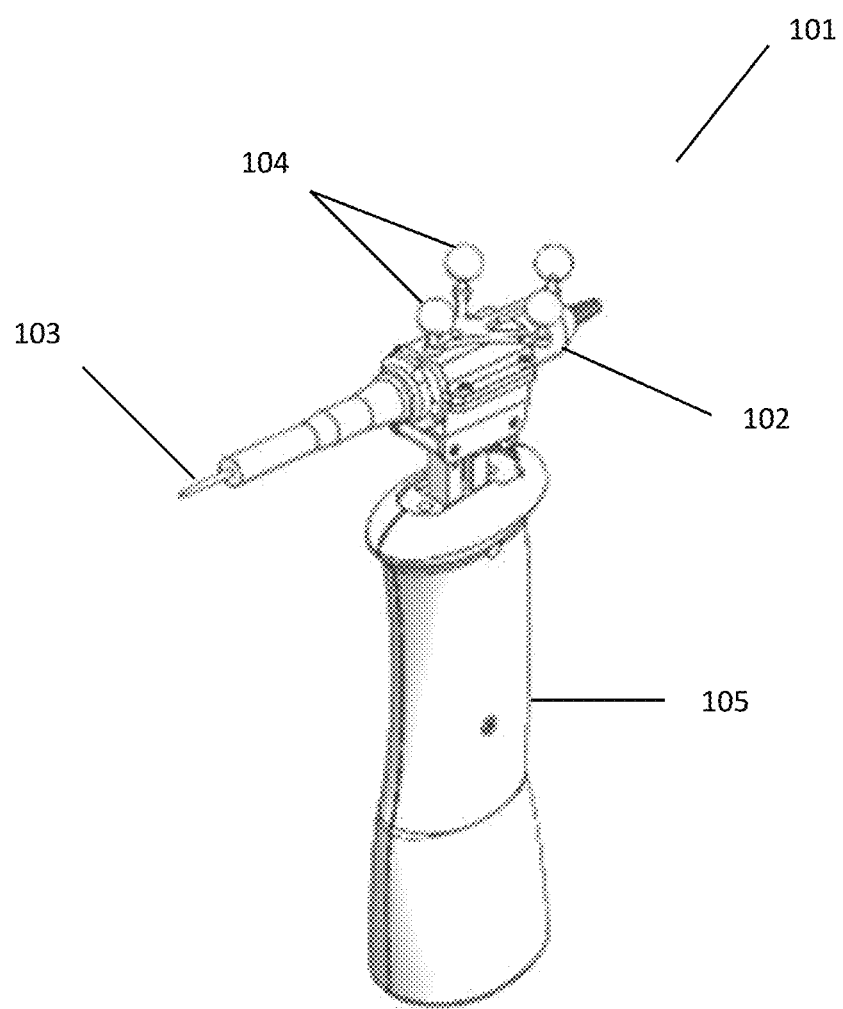
FIG. 2 is an isometric view of an articulating hand-held drill.
Figure 3:
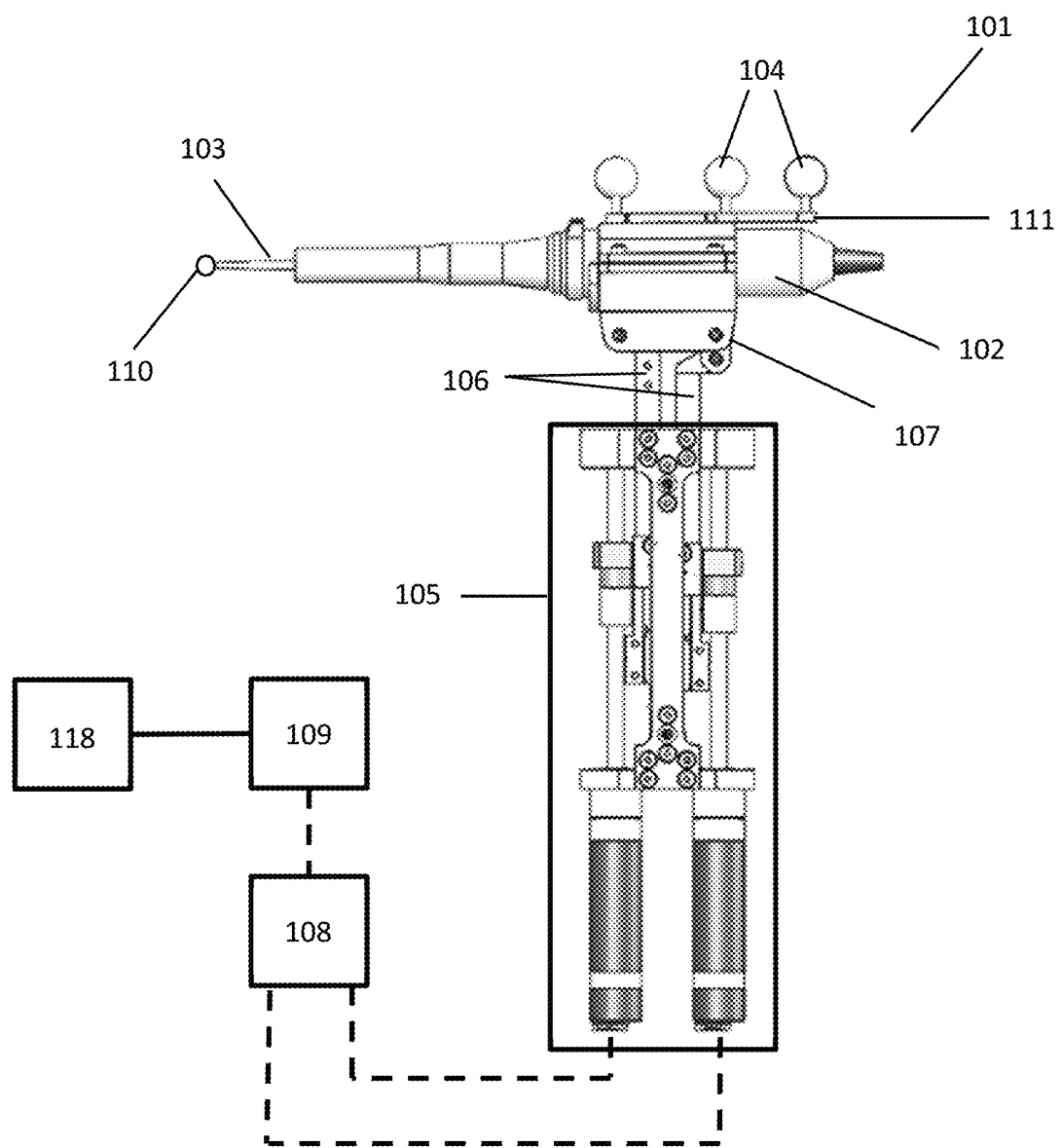
FIG. 3 is a more detailed depiction of the articulating hand-held drill.
Figure 4:
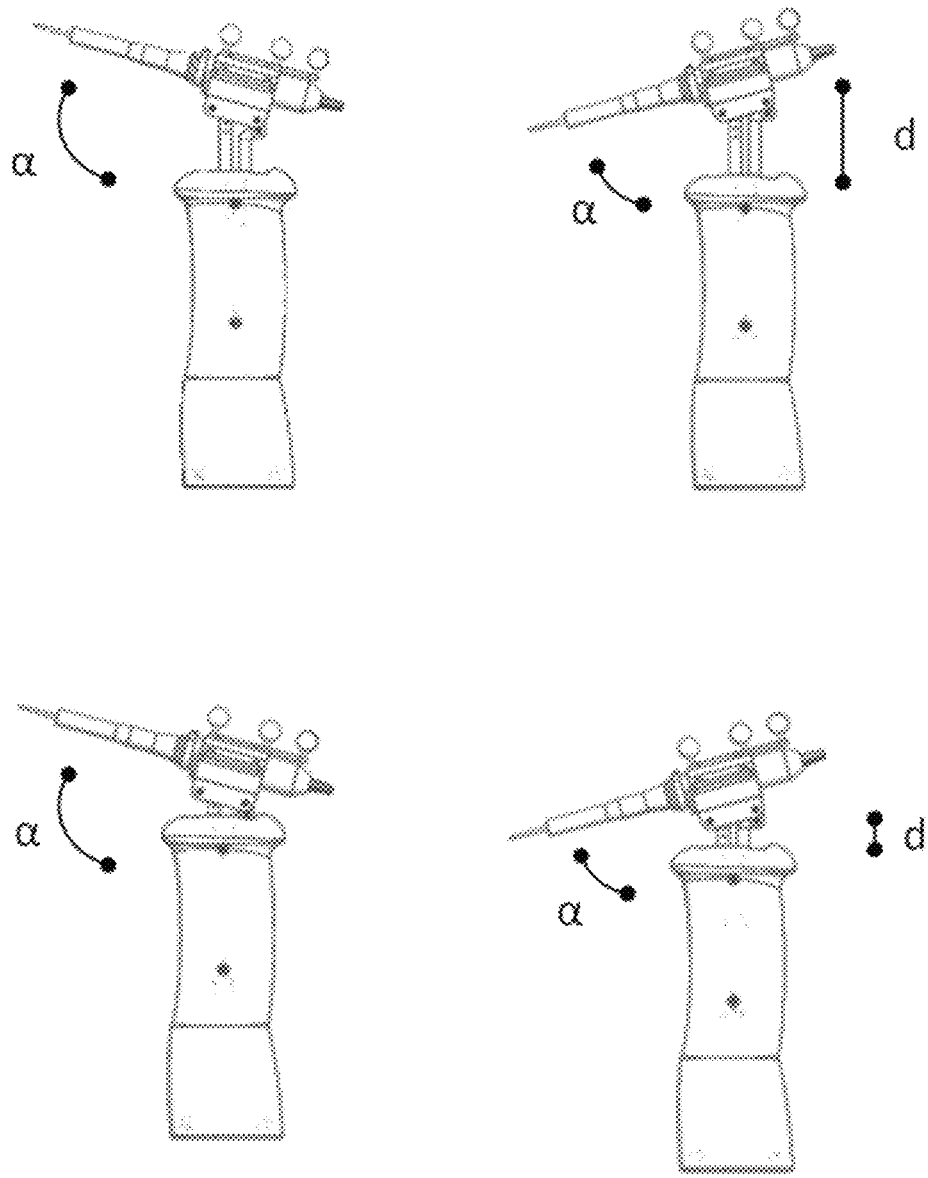
FIG. 4 illustrates the drill portion articulating in two-degrees of freedom.

An inventive articulating hand-held drill system 101 is shown generally in FIG. 2. The main components of which include a handle 105, a drill 102, and drill bit/blade 103. With reference to FIG. 3, the handle comprises at least two rods 106 connected to the drill 102. Henceforth, the rods 106 refer to a rigid component that can be linearly actuated and are attached to the drill portion 102. The rods are linearly actuated by components within the handle 105, to translate and/or rotate the drill 102 in at least 2 degrees of freedom as seen in FIG. 4. The rods controlled by components within the handle 106 maintain the drill bit/blade 103 in a desired plane independent of the orientation of the handle 105. For example, the drill 102 can articulate, either rotate and/or translate represented as α and 'd' in FIG. 4, based on the amount the rods 106 have been actuated with respect to each other. Therefore during a surgical procedure, the desired cut plane can be maintained independent of how the user's hand moves, within limits, after the cutting has started. The system 101 of the present invention may have several applications for cutting any surface or any object where a linear cut or set of cuts are needed. In at least one embodiment the system of the present invention is optimized for cutting the sternum, but is not limited to that use. Other surgical contextual locations that are cut by the inventive system illustratively include a knee joint, hip joint, spine, shoulder joint, elbow joint, ankle joint, jaw, tumor site, joints of the hand or foot, and other appropriate surgical sites or for any osseous cut planes in the same fashion and logistics. Those skilled in the art will appreciate the devices use in a variety of different surgical applications such trauma, orthopedic, neurology, ENT, oncology and the like. Additionally, the system can be used to assist a user in performing surgical operations that require a linear or set of cuts such as but not limited to total hip arthroplasty, total knee arthroplasty, bone osteotomies, spinal surgery, microsurgical scalpel stabilization, plastic surgery, cranial surgeries, and craniofacial. Similarly, it should be appreciated that although the disclosed invention is described for use in a medical setting, other applications for the device can be used wherever an accurate planar cut needs to be achieved and/or planned, such as for making cuts for construction, welding/laser cutting stability, aircraft inspection, bonding compound (e.g. BONDO®) smoothing, carpentry, masonry, soldering, sewing applications, or for creating precise rivet patterns on large work pieces.

Drill

The inventive system 101 provides a mechanism for cutting the intended cutting surface. The construction and types of drill and various cutting bits/blades for cutting the sternum or other osseous tissue are well known in the art. For example, it is known in the art that drill for human tissue and drills for wood, while similar, are distinctly different because of their intended use and differences in sterile requirements. The drill is alternatively a saw, or any other operable cutting device presently known in the art. Commercially available surgical saws include the cardiothoracic DBC and DPX series manufactured by deSoutter Medical, as well as oscillating tip saws used in total hip and knee arthroplasty such as the System 7 Precision Saw manufactured by Stryker. Other types of cutting bits/blades may include burrs, end mills, reamers, cutters, engraving tools, drill extensions, broaches, routers, sanders, and any other tool attachable to a reciprocating or rotary drill/saw 102.

The drill in certain inventive embodiments has a handle 105 configured for holding by a human hand, in addition to one or more adjustments including blade adjustments, handle adjustments, or knob adjustments (not shown) in order to position the drill, its handles, or knobs, particularly to the preference of a user. In at least one embodiment, the drill is hand-held by the operator as a standalone unit with no external constraints capable of receiving and executing actuation commands wirelessly. In other embodiments, the drill and/or its components are electrically connected to external units 108 such as but not limited to computers, processors, controllers, power supplies, navigation system and/or combinations thereof.

Figure 5:
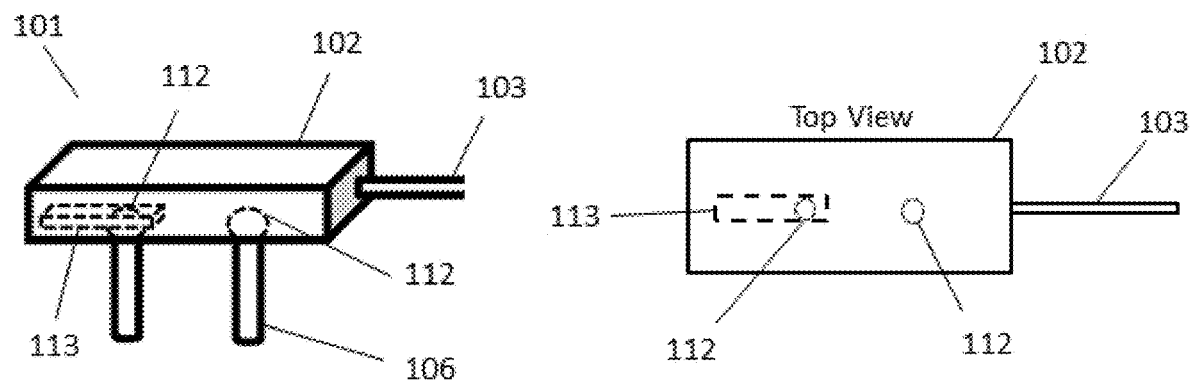
FIG. 5 depicts one proposed connection between the actuators and drill portion of the articulating hand-held drill.

In one embodiment of the device, the rods 106 are attached to the drill 102 by means of a hinge mechanism 107 that allows the drill to move in at least two degrees of freedom. In other embodiments, the rods are attached to the drill by means of a captured sphere 112 where one of the rods is fitted into a sleeve 113 that allows the sphere to slide back and forth as seen in FIG. 5. This allows for optimal movement of the drill as the rods are actuated linearly.

In certain inventive embodiments, the system 101 includes a drill guard. The drill guard 110, when present, travels on the underside of a cutting surface and inhibits the drill bit/blade 103 from cutting any surfaces thereunder. In a surgical context, the drill guard 110 prevents the inadvertent cutting of soft tissue beneath the cutting surface. Drill guards are currently present on surgical saws and come in different configurations. For example, a craniotomy saw has a drill guard having of an angled footed attachment seated below the blade to prevent the damaging of brain tissue when cutting the skull. In one certain embodiment the drill guard 110 is formed of a sphere within a sphere attached to the tip of the drill bit/saw blade 103 that rides along the underside of the sternum while not spinning significantly with the drill rotation to avoid possible friction burns and cutting of soft tissue.

Articulating Drill

The actuation of the rods 106 provide the controlled movement to the drill bit/blade to be fixed along the desired or pre-planned planes. In at least one embodiment, two rods 106 are actuated independently to allow the drill bit/blade 103 to be operated in at least two degrees of freedom. As shown in FIG. 4, if the two rods are actuated in opposing directions the drill rotates, for example, an angle α. If the two rods are actuated in the same direction the drill translates, for example, a distance 'd'. The actuation occurs in real-time adjusting the rods appropriately to maintain the desired cut-plane during cutting. The degree and amount of rotation, α, and/or translation, 'd', depends on the desired cut plane relative to the orientation and position of the handle during cutting. In another embodiment, the drill includes of three or more rods 106 attached to the drill 102 actuated to allow the drill bit/blade to be operated in three degrees of freedom or more. Similarly, the amount each independent rod is actuated controls the desired cut-plane.

The mechanisms for controlling the rods can be achieved by a plurality of components assembled within the handle 105. This can include but not limited to synchronous motors, servo motors, actuator motors, worm drives, gears, screws, bearings, power supply, hydraulic systems, pneumatics systems and/or combinations thereof. The mechanism for actuating the rods 106 can be created by any linear actuator. The components housed within the handle 105 can are orchestrated to control the position and orientation of the drill 102 using signals from controller/s 108 including a microprocessor that may be housed within the device, attached to the device, and/or located externally. In one embodiment, the rods are actuated by two independent linear actuators by two separate controllers 108 receiving signals from a real-time processor 109. A real-time computer 109 provides feedback to controller/s 108 and/or actuating components to maintain the correct plane of the drill bit/blade during cutting based on the position and orientation of the drill portion sensed from the optical tracking system 118. The actuators that maintain the desired plane may also be in direct communication with the navigation system, an operator feedback system, a computer, processor/s and/or combinations thereof.

In a preferred embodiment, the navigation system tracks the position and orientation of the drill portion 102, independent of the handle. A tracking array 111 including active or passive tracking markers 104, is attached to the drill 102. There are specific control advantages to tracking the drill 102 as opposed to the handle portion 105. One advantage is there is no need to calibrate the drill 102 relative to the handle 105 because the drill 102 is the moving portion and is being directly controlled from the rigid handle 105. In other embodiments at least three or more active or passive markers are directly attached to and/or incorporated with and/or within the drill portion 102 to track the drill independent of the handle. In another embodiment the three active markers are configured on a marker array 111 that can be attached to or incorporated with the drill portion 102. The active or passive markers can be arranged on the drill 102 in a plurality of configurations and numbers.

In other embodiments the handle 105 may be tracked by the navigation system or the entire position and orientation of the drill is tracked. In a further embodiment the handle and drill may include independent sets of active and/or passive markers so the two components are tracked relative to one another by one or more navigation system/s.

Figure 7:
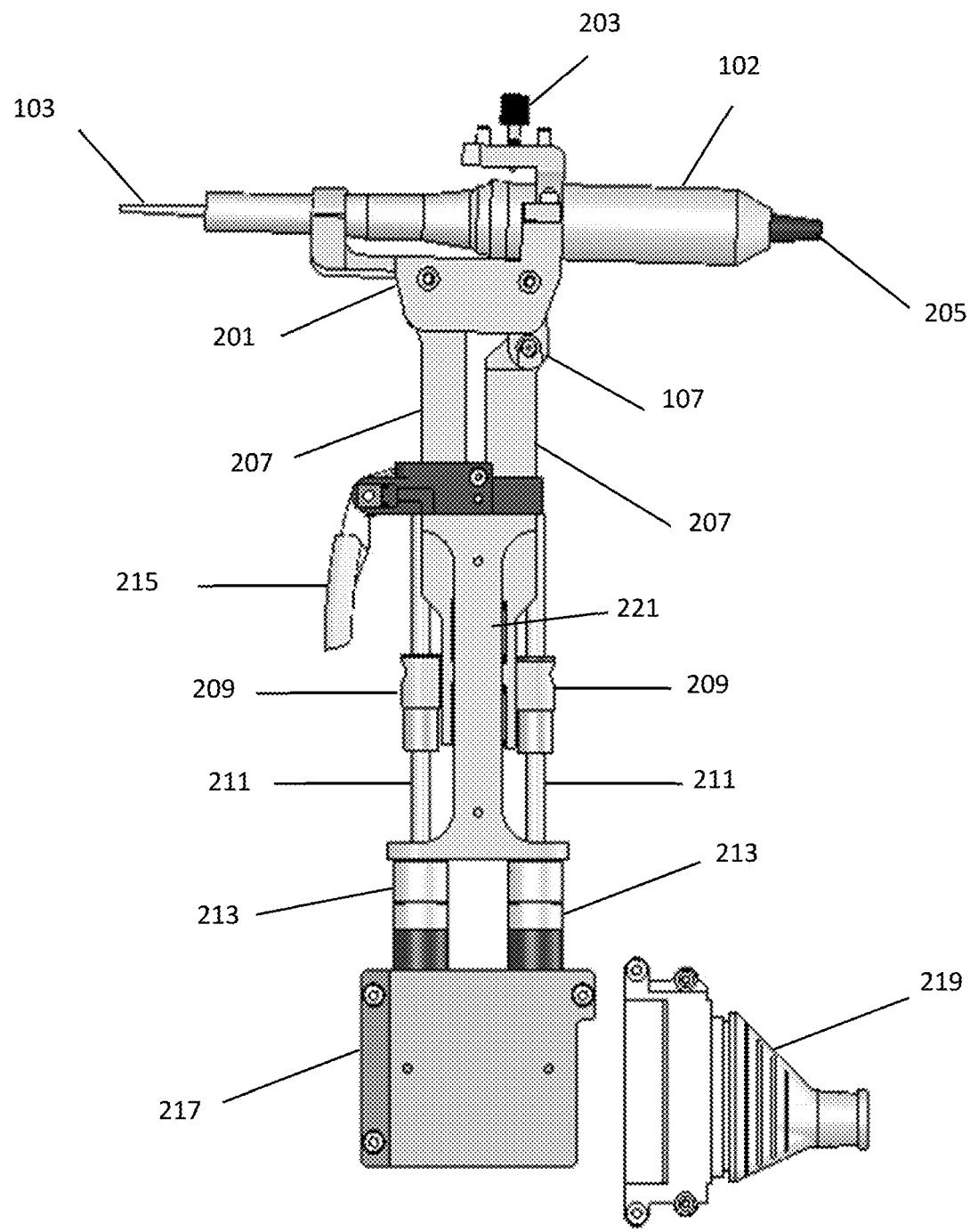
FIG. 7 depicts a preferred configuration of the hand-held drill system.

A more detailed view of the preferred embodiments of the inventive hand-held drill system is shown in FIG. 7. As previously described, the hand-held drill system includes a drill bit/blade 103, and a drill 102 for linearly reciprocating or rotating the drill/bit blade 103. A carriage 201 connects the drill portion with two actuating rods 207. The two rods 207 shown here are linear rails that can slide along a linear guide 221. At the proximal end of the linear rails 207, are screw nuts 209 attached thereto. The screw nuts are in communication with lead screws 211. Servo-motors 213 rotate the lead screws 211 thereby causing the screw nuts 209 to translate along the lead screw axis. The linear rails 207 attached to the screw nuts 209 therefore translate accordingly. Thus, the controllers can control the servo motors to rotate the lead screws 211 to obtain a final position and orientation for the drill portion as previously described.

The two servo motors 213 are encased in a housing 217 for stability. The hand-held drill system in FIG. 7 also includes two electrical input ports 205 and 219. The electrical input port 205 is adapted to receive power and/or motor control inputs for the drill 102. The electrical input 219 is adapted to receive power and/or motor control inputs for the two servo motors 213. In addition, the carriage includes a fixation mechanism 203 to attach or fix a tracking array to the drill portion. Finally, a trigger 215 is incorporated with the hand-held portion to provide a mechanism for user input.

Figure 8:
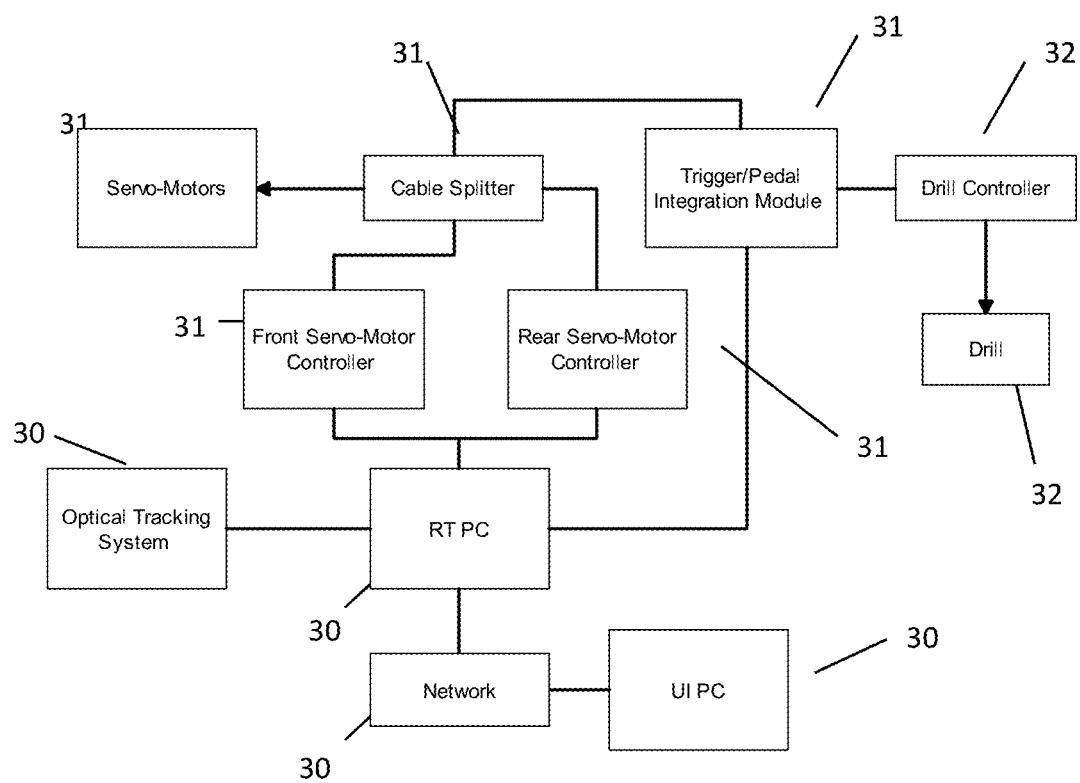
FIG. 8 is a schematic of the external hardware and controls for the hand-held drill system.

A preferred embodiment of the external hardware and controls for of the hand-held drill system is shown in FIG. 8. A real-time computer 301 is programmed to provide a majority of the computational tasks for the system. Data from the optical tracking system 303 is sent to the real-time computer 301 which may calculate the pose of any tracked objects in the operating room. Alternatively, the optical tracking system 303 may compute the pose of the tracked objects and send the position data directly to the real-time computer 301. The measured pose of the drill portion is compared to the desired or pre-planned pose in three-dimensional (3-D) space. The comparison may be made relative to other tracked objects in the operating room, such as a bone with a fixed tracking array. The user may pre-plan a desired plane in the operating room using a user interface computer 305. The user interface computer 305 may be used for a variety of other applications as described herein. The real-time computer 301 and user interface computer 305 may communicate through a wired or wireless network 307.

The real time computer 301 sends control set points to two servo-motor controllers, 311 and 313, to correct for any deviations between the actual measured pose of the hand-held drill portion and the desired position. One servo-motor controller 311 controls the rear servo-motor and the other servo-motor controller 313 controls the front servo-motor. The servo-motor controllers may be for example EPOS motor controllers manufactured by Maxon Precision Motors, Inc. (Fall River, Mass.). The real-time computer 301 also processes user commands from the trigger 215 and/or a foot pedal (described below) from a trigger/pedal integration module 315. Commands from the real time computer 301 and the trigger/pedal integration module are sent to a drill controller 321, which connects to the drill input port 205 to control the drill 102. The drill controller 321 may be for example the BienAir motor controller manufactured by Bien-Air (Bienne Switzerland). The front servo-motor control 313, rear servo-motor controller 311 and trigger/pedal integration module 315 connect to a cable splitter 317. From the cable splitter 317, the servo-motors 213 are controlled accordingly receiving the instructions via electrical input port 219.

Navigation System

In one embodiment of the device, the position and orientation of the drill is tracked to determine its relative location in space and to the patient's anatomy. Many types of navigation systems are available such as the Polaris Optical Navigation system manufactured by NDI or the accuTrack 500 manufactured by Atracsys which utilize cameras to track passive and/or active markers in the surgical field. Similarly, the position and pose of the drill can be tracked using active or passive markers 104 mounted upon the drill 102. The active or passive markers capable of emitting or reflecting optical signals such as visible light, infrared, UV, radio-frequency, sound waves, magnetic fields or any other signal capable of communicating with a navigation system. The optical tracking system 118 of the navigation system can be electrically connected to a real-time processor and/or computer 109 to, in real time, track the position and orientation of the drill 102 and send control signals to the controller 108 that control components in the handle to accordingly actuate the rods in the desired plane. In one embodiment, the optical tracking system can capture the position of the optical markers synchronously. In other embodiments the position of individual optical markers are captured by the optical tracking system sequentially.

In another embodiment of the device, the navigation system also incorporates inertial measurement units such as accelerometers and/or gyroscopes incorporated and/or attached to the drill portion for additional tracking information as to the velocity, position and orientation of the device (not shown). In one embodiment the data from the inertial measurement units can be fused with the data from the optical tracking system in the processor/computer 109 to estimate the position, velocity and orientation of the drill portion using filtering techniques well known in the art, such as Kalman filtering. The inertial measurement units can transmit data through an electrical connection or transmitted wirelessly using WiFi, TCP/IP, UDP, Bluetooth or LiFi connection to a real-time processor and/or computer to receive and process the data. In another embodiment, GPS (not shown) can similarly be used as a method for tracking the drill portion and can be used in association with the optical data from the optical tracking system and the inertial measurement units.

In one embodiment the device is tracked using tracking units such as but not limited to active markers, passive markers, inertial measurement units, GPS and/or any combination thereof. Additionally, the tracking units can come in a plurality of numbers, orientations and positions on the drill to ensure accurate tracking. In another embodiment of the invention, a tracking array 111 including active or passive markers 104 can be electrically connected to the drill and housed at a plurality of locations or can be directly incorporated with the drill portion 102. FIG. 3 depicts an example of the tracking array 111 on the drill portion 102 in one embodiment.

The navigation system provides real-time feedback relating a drilling surface to the position and orientation of the drill 102 during operation. An additional set of tracking units can be attached to the anatomy and provide an anatomical reference frame to monitor any movement of the surface. Additionally, optical markers can be located at a fixed position in the operating room to provide an origin as a coordinate frame of reference for the optical tracking system 118. The navigation system can then detect the drill and anatomy position and orientation to signal any appropriate adjustments to the rods via a controller 108 and/or the components within the handle 105 to maintain the desired plane of cutting. The navigation system including optical tracking, inertial measurement units and/or GPS can communicate with the actuator components housed in the handle 105 either directly or through other devices such as a computer/processor 109, controller 108 so the desired plane is maintained to follow a pre-planned cutting path, compensate for user error and/or anatomical movement and any combination thereof.

In one embodiment, the optical markers 104 are LEDs that can be actuated by a microprocessor located on the drill system 101 capable of actuating the LEDs to transmit data at a high rate. The microprocessor is capable of transmitting a plurality of data types. One example includes the data from the inertial measurement units that can improve the latency of the system and provide a fast tracking mechanism. The drill system 101 may additionally include wireless receivers attached or incorporated in the drill portion 102 and/or the hand-held portion 105 that can receive signals and/or data from a computer, processor, controller or the navigation system to maintain the desired plane of cutting. The receivers can additionally be optical receivers connected to microprocessors attached to or incorporated in the hand-held portion 105 and/or the drill portion 102. The drill system can also include micro-controllers within the hand-held portion 105 and/or the drill portion 102 that receive signals by way of the receivers on the drill system 101 capable of controlling the actuators and can further improve the latency of the system.

In certain inventive embodiments, the system 101 records a pre-indicated cutting pattern or a cutting pattern is taught by an operator prior to operation of the drill. In at least one embodiment, the real-time processor 109 is taught referential points by contacting the drill and/or drill bit/blade 103 tip to operator specified target points. The navigation system that can include an optical tracking system 118, inertial measurement units, and/or GPS can all be used for tracking and setting the desired points and planes specified by the user. In at least one embodiment, the operator specified target points are recorded by one or more computers 109, with one or more computers in communication with the optical tracking system 118, inertial measurement units, GPS and/or an operator-feedback mechanism portion thereof. For example, in an exemplary embodiment, the cutting pattern depicted in FIG. 6 shows a "zigzag" 116 cut path on the anterior portion of the "sternum" 114, but is kept in a straight line 117 on the posterior of the sternum. In one embodiment the user can pre-define the "zigzag" cut path by selecting the corner points 115 of the "zigzag" to be registered and recorded by the computer/processor 109 by way of the navigation system. The operator would then steadily cut a straight line down the middle of the sternum 114. The device would then articulate to keep the drill tip (under the sternum) on the best fit line between the indicated corner points 115 while the drill body passes through the corner points 115 on top in a line-to-line manner. The resulting pattern provides definitive and distinct referencing landmarks and supporting structure to connect the two halves of the sternum post-operation.

In another embodiment, the real-time processor 109 can be connected to another processor/computer or directly to a monitor (not shown) to display information regarding the procedure. The monitor displays information such as, but not limited to, the position of the drill relative to the anatomy, the progression of a procedure, procedural steps, accuracy of the cutting, warnings, safety zones, the intraoperative plan, a pre-operative plan, the depth of the cut, and any combinations thereof. Additionally the user can interface with the monitor by means of a mouse, keyboard, pendant, touch screen, and any combinations thereof. The user interface allows the user to perform a plurality of tasks such as, but not limited to, defining an intra-operative plan, selecting new planes to cut, halt or abort a procedure, change the cutting speed, define cutting planes, placing three dimensional (3-D) virtual implants relative to the anatomy based on cuts that have been performed or want to be performed. In one specific embodiment, a 3-D model of the anatomy is shown on the display and update as parts of the actual anatomy is removed by the drill. The user may then virtually display how the implant may fit on the modified bone before making any proceeding bone alterations. This may be used as a form of real-time intra-operative adjustments during a procedure to accurately fit an implant on the bone. Additionally, the user interface allows the user to send information to the processor/computer 109, the controller/s 108, the optical tracking system 118, the drill system 101, the drill portion 102, other external components and any combination thereof.

Operator Feedback Mechanism

The operating feedback mechanism allows for quick communication from an operator to interact with the inventive system 101. The operating feedback mechanism may alternatively be a system of one or more mechanisms, buttons, switches, and may include one or more computers for interpreting the operator's interaction. In certain inventive embodiments, an operator-feedback mechanism is provided for enabling an operator to communicate with the system for various reasons. In certain inventive embodiments, the operator-feedback mechanism is a trigger or a foot pedal. In certain inventive embodiments, the operator-feedback mechanism can be activated by an operator at any time to communicate to the navigation system and device that the plane of cutting should change from one plane to another such as from zig to zag. The change from one plane to another will match an indication given by user that relates the way the user is holding the device at the time, i.e. the plane that matches the vector through the handle of the device, or the plane that targets a pre-indicated endpoint on another part of the sternum that was indicated before the cutting.

The operator feedback mechanism provides one method to indicate a change in the desired cutting plane. In another embodiment, the real-time processor 109 and optical tracking system 118 can automatically determine from the pre-defined points/planes indicated by the user that the change of the plane has occurred. The optical tracking system knows the location of the anatomy relative to the drill portion and has been taught an intra-operative plan by the user. As the user is cutting and gets to a pre-defined point where the plane is to change, the user can simply change the orientation of the drill portion to the new plane and the real-time processor 109 by way of the optical tracking system 118 can automatically know that the plane has changed and maintain the new plane. Therefore the user wouldn't necessarily need an additional trigger or foot pedal to indicate the plane has changed. In one embodiment, the user can have both the option to have the computer automatically update the new plane, or have the option with a trigger or foot pedal to indicate to the system of a new plane.

In another embodiment, a trigger (not shown) is incorporated to the drill system 101 and can be used by the operator to control the speed of the drill. The amount the trigger is de-pressed can correlate to an increase in the speed of the drill bit/blade 103. The amount the trigger is pulled may have a linear or non-linear relationship as to the speed of the drill bit/blade. The trigger can be located on the hand-held portion 105, or to the drill portion 102. The speed trigger can be in direct communication with the drill portion 102 to control the speed.

Articulation Mechanism

Figure 10:
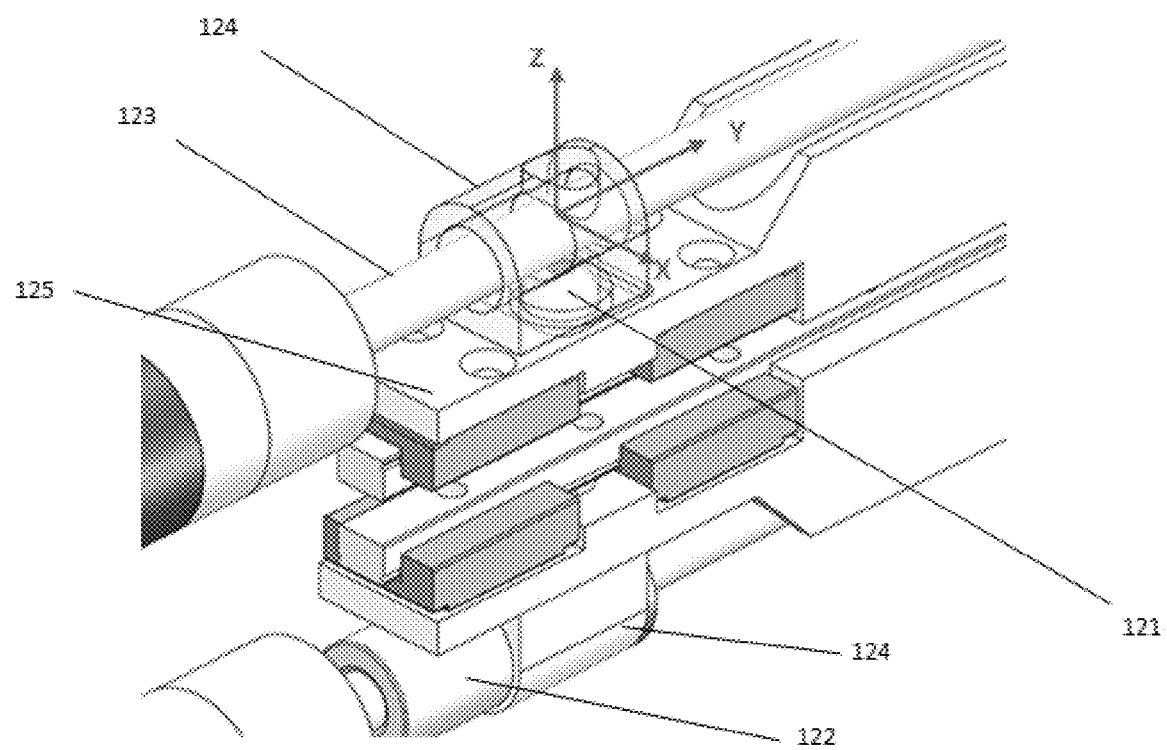
FIG. 10 is a detailed view of a linear rail bearing mechanism of the hand-held drill system.

The manufacturing tolerances and assembly of the components can have a significant effect on the accuracy and performance of the articulating drill. In one embodiment, with reference to FIG. 10, the articulation of the drill portion 102 is created by actuator motors rotating a lead screw 123. A lead screw nut 122 is connected to a compartment 124 that connects to a linear assembly 125. Therefore the lead screw nut 122 is connected to the linear assembly by way of compartment 124 and not directly to the linear assembly 125. Within compartment 124 is a mechanism with a precision spherical component 121 located within a precision fit bore. The mechanism allows for motion in the Z and X axis and rotation around the lead screw and all axes but constrains the motion in the Y direction therefore enabling the transmission of linear motion to articulate the drill-portion appropriately. The purpose of the mechanism is to remove the possible situation of an over constraint lead screw and linear rail assembly due to variation in manufacturing and assembly tolerances.

Reference Guides

Figure 9:
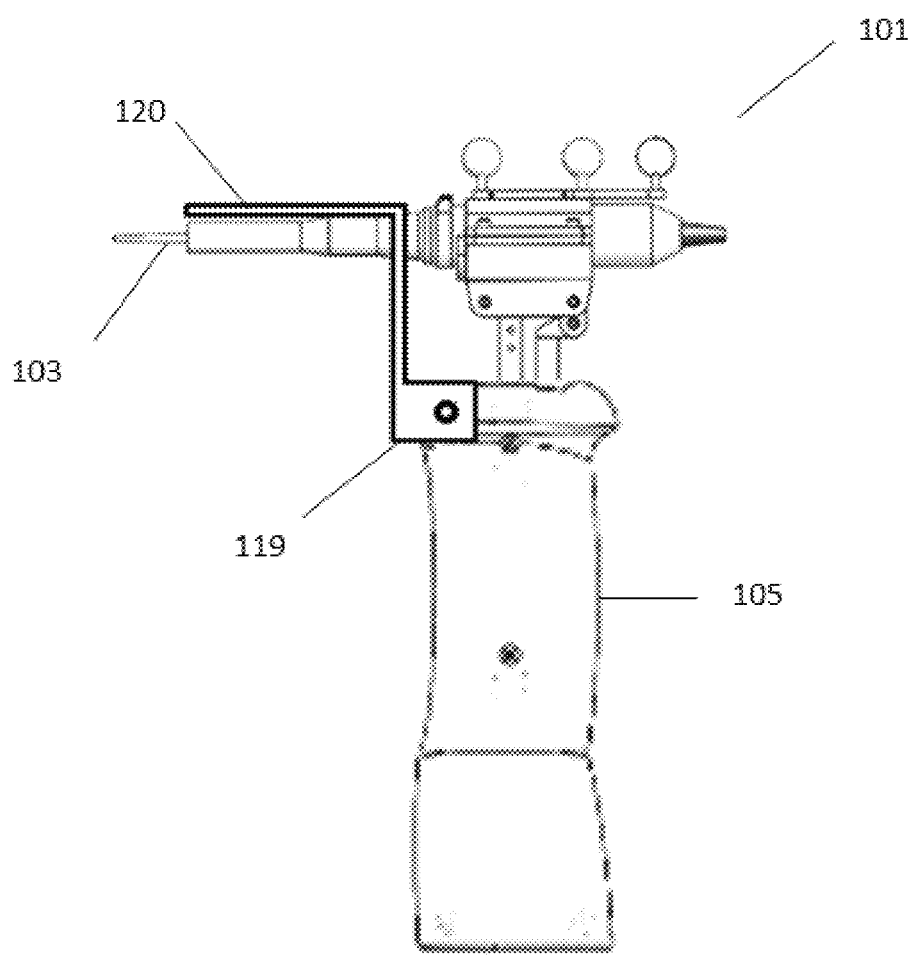
FIG. 9 depicts the articulating hand-held drill with attachable reference guides.

During certain medical procedures, such as total knee arthroplasty, multiple planar cuts need to be made to prepare the tibia and femur for the implant. As the drill bit/blade is driven deeper into the bone, the user has less visibility as to the cut at the tip of the blade. With deeper cuts it becomes more difficult to control the plane in the deeper regions. Therefore a plurality of different attachments can be assembled to the hand-held portion 105 and configured to provide the user with a reference guide with respect to the position and orientation of the drill bit/blade. Referring to FIG. 9, the hand-held portion 105 may include an adapter 119 wherein different types of reference guides 120 are attached to help guide the user. The reference guides provide the user with a visual continuous confirmation process as to the desired plane of the drill bit/blade with respect to the handle. Therefore the user may use the referencing guides to hold the handle in an orientation and position that will aid in maintaining the drill bit/blade in the desired plane. This can be especially useful with deeper cuts where it may be difficult to control the cutting plane. This can also minimize deeper cuts variable trajectory changes from pre-planned optimal cutting plane trajectory.

In one embodiment the referencing guides can be simple rigid objects configured as shown in FIG. 9 attached to both sides of the hand-held portion. In this embodiment, the guides match the plane of the cutting plane but can also protect soft tissues as a user cuts the plane laterally and/or provide a reference as to how deep the drill bit/blade 103 plunges into the bone. The guides may be rigid but pliable to minimize risk to any soft tissue the reference guides may encounter. The guides aid the user by providing a physical referencing plane directly in sight of the surgical site and/or surgical line of sight attached to the hand-held portion relative to the working portion 102.

In another embodiment, the reference guides are provided by a plane of fluid that is propelled in the desired plane. The plane of fluid may also be used to irrigate, control the temperature gradient during cutting, and/or bone chip removal in the surgical site. In one embodiment, fluid conduits can be attached to one and/or both sides of the hand-held portion by way of the adapter 119. The fluid can be routed, or fluid conduits can be assembled, to spray the fluid in a plane that provides the similar visual reference guide as to the desired plane of cutting with the plane of the drill portion with respect to the position and orientation of the hand-held portion. In one embodiment, the plane of fluid can be sprayed in a fan-shape. In another embodiment, the fluid can be sprayed in a straight stream. In other embodiments, one or more streams of fluid are used to provide the visual reference guide in a fan-shape stream/s, straight stream/s and/or combinations thereof. The stream of fluid can be configured to spray from a position above, below, on the side, and/or both sides of the drill bit/blade but aimed to provide the user with a reference between the desired plane of cutting with respect to the position and orientation of the hand-held portion. The fluid may be for example saline, saline with antibiotics, or a fluid with compound/s that would be of benefit to the patient as a certified surgeon would deem appropriate. Additionally, the stream of fluid or a clear plastic reference guide can be illuminated by an LED to provide the user with better visual feedback as to the desired cutting plane.

In other embodiments, a nozzle attached to the end of the fluid conduits can be used to adjust the flow and/or shape of the fluid. For example, the nozzle can be rotated to change the shape of the plane of fluid from a fan-shape to a straight stream. Such nozzles are well known in the art. Similarly, the user can have control by way of a user-feedback mechanism as to whether the fluid is on, off and/or change the velocity of the fluid being propelled into the surgical site.

In another embodiment, the irrigation tubing is replaced by a canister or pressurized compartment that can be attached to the hand-held portion as a stand-alone unit. For example, a container including a fluid compartment and pressurizing compartment in communication that can propel the fluid by means of manual pressurization or from a $CO_2$ canister therefore removing the necessity to have an external pump or bulky irrigation tubes attached to the hand-held device. Therefore the device can still be a wireless stand-alone unit with no external connections to maintain ease of use of the device for the user.

Device Feedback

The use of tactile/haptic, audio and visual feedback for the hand-held drill system can provide the user with additional cues and information for performing a surgery. In one embodiment, the hand-held portion 105 may contain additional actuators, gyroscopes, inertial measurement units, vibrotactile devices that can provide kinematic feedback to the user. There are systems in the art that provide the sensation of force acting on the hand when the device is moving in a particular direction. One such example is the GyroTab being developed by Microsoft Research, which is a hand-held device that provides reactive torque feedback. When the device is translated or rotated in a particular direction, the device provides an opposing reacting force. The hand-held portion 105 may contain similar elements to help guide the user during the procedure for additional stability and/or to aid in finding pre-operative planned planes. The haptic feedback may also be used to guide a user to a safety zone where the drill portion 102 can be engaged as a safety feature of the device.

Tactile feedback can also provide the user with feedback to adjust the hand-held portion to the desired cutting plane by way of a mechanism in communication with the user's hand. In one embodiment, the tactile mechanism is a trigger located on the front of the hand-held potion in communication with a user's finger. In other embodiments, the trigger is located on the back of the hand-held portion in communication with a user's thumb. The trigger can rotate and translate a user's finger indicating the amount of error between the hand-held portion and the cutting plane of the drill portion. If the hand-held portion is oriented or positioned an angle or distance from the desired cutting plane, the trigger will provide the user with feedback to adjust the hand-held portion by rotating and/or translating in the direction the hand-held portion needs to be adjusted to maintain the plane. In other embodiments, the trigger can comprise a rotational portion on the trigger that rotates to provide the user with tactile feedback to adjust the hand-held portion accordingly to maintain the cutting plane. The speed, direction and/or continual rotation of the rotational portion on the trigger can indicate the amount, direction, and/or degree the hand-held portion needs to be adjusted to maintain the cutting plane. The trigger can also translate to provide the user with tactile feedback to adjust the hand-held portion to minimize translational error between the hand-held portion and the desired cutting plane.

The tactile feedback can also be provided by a mechanism that is connected to the drill portion and to the hand-held portion in communication with a user's hand. In one embodiment, one end of a rigid structure such as a bar or rod is fixed perpendicular to the drill portion. The other end of the rigid structure is perpendicularly fixed to one end of a flexible material such as Nitinol. The other end of the flexible material is fixed to the hand-held portion which is in communication with the user's hand. The mechanism provides the user with feedback as to the plane of the drill portion relative to the hand-held portion. If the position and/or orientation of the hand-held portion deviates from maintaining the desired cutting plane, the flexible material will bend on the user's hand or fingers providing force feedback to adjust the hand-held portion in the opposing direction of the force. No force from the flexible material would indicate the hand-held portion is correctly aligned to maintain the drill portion in the desired cutting plane.

In other embodiments, the tactile feedback mechanism on the hand-held portion in communication with the user's hand can provide information as to a new plane of cutting based on a pre-operative or intra-operative plan. For example, when the user reaches a target point to change the plane of cutting, the trigger, capable of providing translational and rotational feedback, can indicate to the user the position and orientation of the new plane. The trigger can be in communication with the real-time processor to facilitate the feedback to the user by way of mechanisms within the hand-held portion.

In another embodiment, audio feedback can be provided by the system to assist the user for a variety of different purposes. For example but not meant to be limiting, the system may notify the user when the correct plane or plane density has been found or reached, notify the user to change planes, warn the user if the drilling portion is outside of certain limits or are approaching limits the system can no longer adjust for, etc. The sounds can be any audible signal such as a beep, variable beeping sequence, audible voice of a certain language or dialect, or combination of sounds that can convey the message to the user. Different sounds can be associated with different functions. Additionally, the audible sounds may be associated with messages or signals that are prompted on a monitor.

In one embodiment, the system includes visual feedback. In addition to or in substitution of the monitor connected the real-time processor, the user may wear a pair of glasses. The glasses with embedded elements or external elements capable of displaying a plurality of visual data to the user during a procedure. The glasses may be in electrical and/or wireless communication to receive signals from the real-time processor 109, the optical tracking system 118, the drill system 101, the drill portion 102, another external device and any combinations thereof. The types of data that can be viewed by the user may include but not limited to the progress of the procedure, a previous procedural step, a current procedural step, a future procedural step, the accuracy of the planar cut, warnings that the device is out of working range, guidance to a particular plane, a superimposed model of the individual anatomy, a superimposed model of a pre-operative or intra-operative plan, etc.

Safety and Sterility

Usability and safety of using an articulating hand-held drill system is critical in a medical setting. In one embodiment of the device, a safety check and/or volume is created so the drill can only be engaged when it is intended. For example, the real-time processor/computer 109 will only send signals to the controller 108 and actuating components within the handle 105 when the drill portion is in an appropriate safety volume within a clinically safe range surrounding the plane defined intra-operatively or pre-operatively. The navigation system, utilizing patient specific data in connection with the real-time processor can determine if the drill portion is in the appropriate volume and/or desired plane. In another embodiment a light or warning signal can be incorporated on the drill system 101 that turns green indicating to the user that the drill is operable and within the safe zone, or a red signal indicating the drill bit/blade is inoperable and outside of a safe zone. The signal may be in the form of an LED light or display attached or incorporated onto the drill portion 102 or handle 105. An additional embodiment can provide audio cues that the drill portion 102 is in the safe volume or non-safe portion. The audio cues can be in the form of a beep, series of beeps, a changing tempo of beeps or variable sequence of target proximity annotation, voice recording, or any other reasonable arrangement of audio signals to indicate safe vs. non-safe zones.

Any medical device has to be sterile or have a sterile barrier to reduce any risk of infection to the patient. In one embodiment, a sterile barrier can be draped over the drill system 101 wherein the drill bit/blade 103 can be removed from the drill portion 102 to be sterilized or disposed of. In another embodiment, the entire drill portion 102 can be detached from the hand-held portion 105 to be disposed of or disassembled and properly sterilized. The materials of the device that may come into contact with the patient shall be made of biocompatible materials known in the art to ensure patient safety. Additionally any components for re-use shall be capable of sterilization by methods well known in the art.

Other Applications

The hand-held drill system described herein can be utilized for other applications by changing the drill bit/blade with different functional end effectors. The drill bit/blade 103 can be replaced with a tool for creating visual markings on the bone, such as a surgical marker or pen. Considering the necessity for making precise planar cuts in different surgical applications the device can be used for outlining or marking a particular plane on a bone to be cut that aids a surgeon in defining surgical cuts, and intra-operative planning. There are many devices that attempt to define the tibial and femoral cuts to restore the mechanical axis of the knee. The devices mark location where cuts should be made and can be bulky extruding from the surgical site of the knee joint and externally connecting to the talus to correctly mark the alignment of the cut. The drill system with the adapted visual marker instead of the drill/bit blade can define cut locations very accurately based on the accuracy of the optical tracking system with the markers attached to the drill portion relative to the markers attached to the anatomy. In one embodiment, the drill system with the visual marker tip can be used to create cross hairs as to the position and orientation of the keel of a tibial implant in total knee arthroplasty. Additionally, specific to total knee arthroplasty, after a surgeon has made the distal femoral cut, the drill system can be used to mark a line to accurately place a four in one cutting block to finish the rest of the procedure with manual instruments.

In other embodiments of the invention, the drill bit/blade 103 can be replaced with a tool to allow for the articulating drill system to be used for digitizing and/or registering to match a plurality of different coordinate frames with respect to each other. The drill system can be used to register for example but not meant to be limiting, pre-operative patient data, such as from MRI or CT, CT/MRI fusion data, intra-operative data, such as fluoroscopy, 3D simulated models of a patient's anatomy, patient specific 3D anatomical model and general 3D models of anatomy, the location and orientation of optical markers and/or trackers with respect to a patient's anatomy, to calibrate the optical tracking system coordinate frame, to designate specific points in an operating room relative to a patient's anatomy and/or relative to an optical tracking system and/or relative to optical markers or trackers, etc. One skilled in the art would appreciate the functionality of utilizing the hand-held device for matching various coordinate frames relative to each other within a medical setting. The registration can be achieved by changing the drill bit/blade with a rod comprising a semi-sharp tip, or small ball probe, to locate and register specific points on the objects that allows the real-time processor 109 to match the coordinate frames of the various objects with respect to each other to allow for the accurate tracking of each of the objects during a surgical procedure.

In another embodiment, the articulating drill system can be used in a compliant mode such that the drill system can be used for methods other than cutting. Compliant mode may be activated for registration as described above. Additionally, compliant mode may be used, in conjunction with a different tool attached to the drill portion other than a drill bit/blade to contour and define a surface that can be modeled and/or stored in a computer. By placing the new tip and dragging it along a surface, the curves, undulations, contours, etc. can be sensed by the tool and recorded by a processor/computer. As long as the tool tip is in contact with the surface, during the recording process, the drill portion will move with respect to how the surface moves. The method may be used to re-create and define the surface. The approach may also be used as a fast way to register irregular anatomy with the coordinate frames of other objects within the room or with the coordinate frame of markers/trackers attached to that particular anatomy.

Attachments

In another embodiment of the device, other attachments can be placed onto the drill system 101 that provides the user additional support to hold the handheld system. An extension to the bottom of the hand-held portion can allow the user to use two hands to operate the articulating drill providing more stability and control. In another embodiment, a surgical glove that the user can wear directly interacts with the hand-held portion that provides additional stability for manipulating the drill system. The glove may include a locking mechanism that supports the hand in the desired plane of cutting that can be adjusted accordingly when the user needs to change planes. Additionally, the glove can include guides or notches, for example, on the forefinger of the glove that the hand-held portion can align with to provide an additional referencing guide as to the desired plane of cutting and optimal hand held—user ergonomics. This is important for surgeons' safety and demanding cases.

In another embodiment, fluid conduits can be attached to the hand-held portion by way of the adapter 119 that can propel fluid into the surgical site but not necessarily to provide a reference plane as described previously. In this embodiment, the user can propel fluid at different locations in the surgical site by adjusting the hand-held portion 105, while the navigation system and actuators maintain the drill potion 102 in a desired cut plane. Therefore the user can irrigate, chip bone, or visually clear other locations in the surgical site within the limits of α and 'd' in FIG. 4 of the drill system 101, while the drill portion 102 maintains the desired cut path. The fluid conduits can be attached to the outer surface of the hand-held portion such as by way of adapter 119 and/or there can be an attachment for external fluid conduits to fluid conduits housed within the hand-held portion. For example, one or more fluid conduits can be attached to one or more ports at the bottom of the hand-held portion that provides a fluid connection with conduits within the hand-held portion. The internal conduits are connected to an exit port or nozzle on the hand-held portion that faces the surgical site. The user may indicate with a user feedback-mechanism like those described previously to turn the fluid on, off, and/or control the velocity of fluid.

Two Degrees of Freedom vs. Three Degrees of Freedom

There are different advantages to having a device that operates in two degrees of freedom and of a device that operates in three degrees of freedom in terms of surgical technique, control advantages, ergonomics, etc. For a two degree of freedom device, the kinematics are more simple, the motors used in the handle 105 can be larger, and the range of motion in the two degrees can be greater without compromising an ergonomical design when compared to a three degree device. However, a three degree of freedom device would provide a user with an additional degree of movement. For example, when cutting the sternum using a three degree of freedom device, the orientation of the drill can be controlled to be normal to the plane of the sternum at all times. The surgeon can indicate that the plane is to change while cutting and the device is capable of doing so, thus the transition points will not present a discontinuity of the drill orientation in making the planar change. For a two degree of freedom device, however, the orientation of the next plane can be determined as the orientation of the drill at the point where the planar transition is made, since the normality of the orientation relative to the sternum is not particularly critical, as long as it is within a clinically acceptable standardized range.

EXAMPLES

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Example 1

In cardiac surgery use the inventive system is used. The system includes an articulating hand-held drill tracked by a navigation system, where the device can articulate to keep the drill in a fixed plane of motion during a cut through a patient's sternum, independent of how the surgeon's hand moves, within limits, after the cutting is started. The surgeon uses trackable markers or reference devices mounted on the device itself, and on the bony anatomy on the sternum to compensate the cutting pattern for the movement of the sternum due to a patient's breathing in order to preserve a high accuracy and consistency cut.

The surgeon begins cutting along the first plane of the cut. The surgeon reaches the desired area where the surgeon would like to alter the cut to a zigzag pattern and indicates to the device, by pulling a trigger that the plane of cutting should change.

A drill guard is used, located beyond the tip of the drill, riding along the underside of the sternum as the bone is cut, such that the drill will not cut into soft tissue below the bony anatomy. The surgeon begins to cut in a zig direction while the articulating maintains the movement of the drill along the same precise direction, compensating for any deviations that may occur by the surgeon movement during the cut. The surgeon pulls a trigger on the drill, indicating to the navigation system to allow the surgeon to change directions in to the zag direction. The navigation system communicates to the actuating components that will maintain the plane in the zag direction and preventing the surgeon from going back in the zig direction unless, and until, another operator feedback mechanism is used. The surgeon repeats this process along the length of the sternum. Upon completion the zig zag pattern is found to make closing the sternum after cardiac surgery has completed, much easier to perform and stable. Additionally, by using the above example, the surgeon can optimize osseous consolidation and potentially minimize sternum rewiring reoperations.

Example 2

The procedure of Example 1 is re-performed, however a pre-indicated endpoint is used and the pattern is pre-indicated by the surgeon before cutting by touching the tip of the device to a pattern drawn out by the surgeon on the patient's sternum. Upon completion the pre-indicated pattern is found to make closing the sternum after cardiac thoracic surgery has completed, much easier to perform and stable.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. An articulating drill system comprising:
   a hand-held portion;
   a drill portion;
   at least two motors assembled with other components that convert rotational motion to linear motion to adjust a distance and angle of the drill portion relative to the hand-held portion, wherein the linear motion is along an axis substantially parallel to a longitudinal axis of the hand-held portion;

a navigation system for controlling said at least two motors; and at least three markers attached to, or incorporated with, said drill portion to permit the navigation system to track the drill portion independent of a position and orientation of the hand-held portion.

2. The system of claim 1 wherein the navigation system comprises an optical tracking system in communication with one or more real-time processing computers.

3. The system of claim 1 wherein the at least two motors are housed in the hand-held portion.

4. The system of claim 1 further comprising a tool operated by the drill portion, wherein the tool has a tool axis that remains non-parallel to the axis of the linear motion.

5. The system of claim 4 further comprising a motor housed in the drill portion to rotate to the tool.

6. The system of claim 5 wherein the tool is configured to interact with patient tissue.

7. The system of claim 1 further comprising a front controller and a rear controller in communication with the navigation system, wherein the at least two motors comprise a front motor controlled by a front controller and a rear motor controlled by a rear controller.

8. The system of claim 1 wherein the at least two actuators is no more than two linear actuators to control the drill portion in two-degrees-of-freedom.

9. The system of claim 1 wherein the at least three markers are configured on a marker array, wherein the marker array is attached to the drill portion.

10. The system of claim 1 wherein the at least three markers are directly attached or incorporated on the drill portion.

11. The system of claim 1 further comprising at least one light emitting diode (LED) marker attached or incorporated on the drill portion for transmitting data, wherein a microcontroller actuates the LED marker to transmit data to the navigation system.

12. An articulating drill system comprising:
a hand-held portion;
a drill portion;
a front actuator and a rear actuator for adjusting a plurality of degrees-of-freedom of said drill portion relative to the hand-held portion;
a front screw actuated by the front actuator, a rear screw actuated by the rear actuator, a front screw nut assembled to the front screw to translate along the front screw upon rotational motion of the front screw, and a rear screw nut assembled to the rear screw to translate along the rear screw upon rotational motion of the rear screw;
a navigation system for controlling said front actuator and said rear actuator; and
at least three markers attached to, or incorporated with, said drill portion to permit the navigation system to track the drill portion independent of a position and orientation of the hand-held portion.

13. The system of claim 12 further comprising a front linear rod having a first end assembled to the front screw nut and an opposing end assembled to the drill portion, a rear linear rod having a first end assembled to the rear screw nut and an opposing end assembled to the drill portion, wherein the front linear rod and rear linear rod translate independently upon rotation of either the front screw or the rear screw to control at least two-degrees-of-freedom of the drill portion.

14. The system of claim 13 wherein either the opposing end of the front linear rod or rear linear rod are assembled to the drill portion by way of a hinge mechanism.

15. The system of claim 13 wherein the translation of the front linear rod and second linear rod is along an axis that is substantially parallel to a longitudinal axis of the hand-held portion.

16. The system of claim 15 further comprising a tool operated by the drill portion, wherein the tool has a tool axis that remains non-parallel to the axis of the translation of the drill portion.

17. The system of claim 16 further comprising a motor housed in the drill portion to rotate the tool.

18. The system of claim 17 wherein the tool is configured to interact with patient tissue.

* * * * *